United States Patent [19]

Hefner et al.

[11] Patent Number: 5,684,188
[45] Date of Patent: Nov. 4, 1997

[54] CONTINUOUS HETEROGENEOUSLY CATALYZED GAS-PHASE OXIDATION OF PROPYLENE TO ACROLEIN, ACRYLIC ACID OR A MIXTURE THEREOF

[75] Inventors: Werner Hefner, Lampertheim; Otto Machhammer, Kirchheim; Hans-Peter Neumann, Ludwigshafen; Andreas Tenten, Maikammer; Wilhelm Ruppel, Frankenthal; Herbert Vogel, Ludwigshafen, all of Germany

[73] Assignee: BASF Aktiengesellschaft, Ludwigshafen, Germany

[21] Appl. No.: 611,790

[22] Filed: Mar. 6, 1996

[30]  Foreign Application Priority Data

Mar. 10, 1995 [DE] Germany .................. 195 085 32.9
Jul. 13, 1995 [DE] Germany .................. 195 255 06.2

[51] Int. Cl.$^6$ .......................... C07C 45/34; C07C 51/23
[52] U.S. Cl. ............................ 562/532; 568/475; 568/476
[58] Field of Search ................. 562/532; 568/475, 568/476

[56]  References Cited

U.S. PATENT DOCUMENTS

| | | | |
|---|---|---|---|
| 3,198,750 | 8/1965 | Callahan | 252/456 |
| 3,251,899 | 5/1966 | Callahan | 260/680 |
| 3,308,151 | 3/1967 | Callahan | 260/465.3 |
| 3,428,674 | 2/1969 | Callahan | 260/533 |
| 3,475,488 | 10/1969 | Kurats et al. | 260/533 |
| 3,657,420 | 4/1972 | Mancy et al. | 424/121 |
| 3,736,355 | 5/1973 | Croci | 260/530 N |
| 3,778,386 | 12/1973 | Takenaka et al. | 252/432 |
| 3,801,634 | 4/1974 | Krabetz et al. | 260/533 N |
| 3,865,873 | 2/1975 | Oda et al. | 260/530 N |
| 3,867,345 | 2/1975 | Koberstein et al. | 260/530 N |
| 4,031,135 | 6/1977 | Engelbach et al. | 260/530 N |
| 4,049,577 | 9/1977 | Childress et al. | 252/443 |
| 4,129,600 | 12/1978 | Childress et al. | 260/604 R |
| 4,147,885 | 4/1979 | Shimizu et al. | 562/535 |
| 4,224,187 | 9/1980 | Vanderspurt | 252/437 |
| 4,267,386 | 5/1981 | Vanderspurt | 568/480 |
| 4,837,360 | 6/1989 | Kadowaki et al. | 562/546 |
| 5,198,578 | 3/1993 | Etzkorn et al. | 562/532 |
| 5,218,146 | 6/1993 | Takata et al. | 562/535 |

FOREIGN PATENT DOCUMENTS

| | | |
|---|---|---|
| 2157631 | 6/1995 | Canada . |
| 2157632 | 6/1995 | Canada . |
| 0 117 146 | 8/1984 | European Pat. Off. . |
| 0 253 409 | 1/1988 | European Pat. Off. . |
| 0 257 565 | 3/1988 | European Pat. Off. . |
| 0 293 224 | 11/1988 | European Pat. Off. . |
| 0 361 372 | 4/1990 | European Pat. Off. . |
| 1 205 502 | 6/1966 | Germany . |
| 1 468 429 | 1/1969 | Germany . |
| 1 924 431 | 1/1970 | Germany . |
| 1 793 302 | 7/1971 | Germany . |
| 2 009 172 | 9/1971 | Germany . |
| 2 056 614 | 6/1972 | Germany . |
| 22 51 364 | 5/1973 | Germany . |
| 2 202 734 | 7/1973 | Germany . |
| 24 36 818 | 2/1976 | Germany . |
| 27 29 841 | 1/1979 | Germany . |
| 29 43 707 | 5/1980 | Germany . |
| 30 02 829 | 7/1980 | Germany . |
| 30 06 894 | 9/1980 | Germany . |
| 44 31 949 | 3/1995 | Germany . |
| 44 31 957 | 3/1995 | Germany . |
| 0971038 | 9/1964 | United Kingdom . |
| 1035147 | 7/1966 | United Kingdom . |
| 1208848 | 10/1970 | United Kingdom . |
| 1220568 | 1/1971 | United Kingdom . |
| 1337865 | 11/1973 | United Kingdom . |
| 1360819 | 7/1974 | United Kingdom . |
| 1390525 | 4/1975 | United Kingdom . |
| 1 450 986 | 9/1976 | United Kingdom . |
| 1507038 | 4/1978 | United Kingdom . |
| 2037603 | 7/1980 | United Kingdom . |
| 2044764 | 10/1980 | United Kingdom . |

*Primary Examiner*—Joseph McKane
*Attorney, Agent, or Firm*—Oblon, Spivak, McClelland, Maier & Neustadt, P.C.

[57]  ABSTRACT

In a process for the continuous heterogeneously catalyzed gas-phase oxidation of propylene to acrolein, acrylic acid or a mixture thereof in an oxidation reactor whose feed gas mixture comprises, apart from propylene and molecular oxygen as oxidant, only at least one diluent gas which is essentially inert under the conditions of the heterogeneously catalyzed gas-phase oxidation and where, in continuous operation, at least a part of the essentially inert diluent gases present in the product gas mixture is separated off therefrom and is reused as a constituent of the feed gas mixture to the oxidation reactor, the essentially inert diluent gas mixture comprises more than 85% by volume of at least one saturated hydrocarbon having from 1 to 5 carbon atoms.

10 Claims, No Drawings

CONTINUOUS HETEROGENEOUSLY CATALYZED GAS-PHASE OXIDATION OF PROPYLENE TO ACROLEIN, ACRYLIC ACID OR A MIXTURE THEREOF

The present invention relates to a novel process for the continuous heterogeneously catalyzed gas-phase oxidation of propylene to acrolein, acrylic acid or a mixture thereof in an oxidation reactor whose feed gas mixture comprises, apart from propylene and molecular oxygen as oxidant, only at least one diluent gas which is essentially inert under the conditions of the heterogeneously catalyzed gas-phase oxidation, where, in continuous operation, at least a part of the essentially inert diluent gas constituents present in the product gas mixture is separated off therefrom and is reused as a constituent of the feed to the oxidation reactor.

Acrylic acid is an important chemical feedstock which is used, inter alia, as monomer for the preparation of polymers which, for example, are used in aqueous dispersion as binders. Acrolein is an important intermediate, for example in the preparation of glutardialdehyde, methionine, folic acid and acrylic acid.

It is generally known that acrylic acid can be prepared by heterogeneously catalyzed gas-phase oxidation of propylene using molecular oxygen over catalysts which are present in a solid aggregate state (cf., for example, DE-A 19 62 431, DE-A 29 43 707, DE-C 1 205 502, EP-A 257 565, EP-A 253 409, DE-B 22 51 364, EP-A 117 146, GB-B 1 450 986 and EP-A 293 224).

The catalysts used are normally oxide compositions. The catalytically active oxide composition can contain, apart from oxygen, only one other element or more than one other element (multielement oxide compositions). The catalytically active oxide compositions used are particularly frequently those comprising more than one metallic, in particular transition metal, element. These are referred to as multimetal oxide compositions. The multielement oxide compositions are usually not simple physical mixtures of oxides of the elemental constituents, but heterogeneous mixtures of complex poly-compounds of these elements.

In general, the heterogeneously catalyzed gas-phase oxidation of propylene to acrylic acid is carried out at elevated temperature (normally a few hundred ° C., typically from 200° to 450° C.).

Since the heterogeneously catalyzed gas-phase oxidation of propylene to acrylic acid is strongly exothermic, it is advantageously carried out in a fluidized bed or in multitube fixed-bed reactors where a heat exchange medium is passed through the space surrounding the contact tubes. The latter procedure is the preferred one (cf., for example, DE-A 44 31 957 and DE-A 44 31 949). The working pressure (absolute pressure) is normally from 1 to 10 bar. The target reaction occurs during the residence time of the reaction gas mixture in the catalyst charge through which it is passed.

As is generally known to those skilled in the art, the heterogeneously catalyzed gas-phase partial oxidation of propylene to acrylic acid proceeds essentially in two steps in succession along the reaction coordinate, of which the first leads to acrolein and the second from acrolein to acrylic acid. As a result, if the process of the invention is suitable for the preparation of acrylic acid from propylene by gas-phase catalytic oxidation, it is automatically also suitable for the preparation of acrolein from propylene by gas-phase catalytic oxidation, since the preparation of acrylic acid can at any time be stopped at the acrolein stage. Furthermore, the fact that the reaction proceeds in two temporally successive steps makes it possible to carry out the preparation of acrylic acid from propylene by gas-phase catalytic oxidation in two successive oxidation stages, with the oxidic catalyst used in each of the two oxidation stages being able to be optimally matched. Thus, for the first oxidation stage (propylene→acrolein), preference is generally given to a catalyst based on multimetal oxides containing the element combination Mo—Bi—Fe, while for the second oxidation stage (acrolein→acrylic acid) preference is normally given to catalysts based on multimetal oxides containing the element combination Mo—V. Appropriate multimetal oxide catalysts for the two oxidation stages have been described many times and are well known to those skilled in the art. For example, page 5 of EP-A 253 409 refers to appropriate US patents. Favorable catalysts are also disclosed by DE-A 44 31 957 and DE-A 44 31 949, particularly in the form of multimetal oxide compositions of the general formula I. In general, the product mixture of the first oxidation stage is transferred without intermediate treatment to the second oxidation stage. The simplest implementation form of the two oxidation stages therefore comprises a tube-bundle reactor within which the catalyst charge changes appropriately along the individual contact tubes at the end of the first reaction step.

However, the two oxidation stages can also be implemented in the form of an oxidation reactor comprising two oxidation reactors in series. In this case, the other reaction conditions, e.g. the reaction temperature, can be optimally matched in a simple manner to the respective oxidation stage. The molecular oxygen required for the second oxidation stage is here advantageously fed only to the second oxidation reactor. However, in principle, the heterogeneously catalyzed gas-phase partial oxidation of propylene to acrylic acid can also be carried out in a single stage. In this case, both reaction steps occur in one oxidation reactor which is charged with a catalyst and catalyzes both reaction steps. Of course, the catalyst charge can also change continuously or abruptly along the reaction coordinate within an oxidation stage.

All the abovementioned design variants have in common that, owing to the pronounced exothermic character of the partial oxidation of propylene, the oxidation reactors are customarily fed with a gas mixture which contains the reactants molecular oxygen and propylene diluted with a gas which is essentially inert under the conditions of the gas-phase catalytic partial oxidation. Here, diluent gases are those whose constituents remain unaltered to an extent of more than 95 mol %, preferably more than 98 mol %, under the conditions of the heterogeneously catalyzed gas-phase partial oxidation. Usually, the inert diluent gas comprises the major proportion by volume of the three constituents of the feed gas mixture.

The above measure acts counter to the desire for as high as possible a space-time yield of the desired target compound, i.e. there is interest in making the proportion by volume of the reactants in the feed gas mixture as high as possible. Here, the proportion by volume of the molecular oxygen to be used as oxidant in the feed gas mixture is of particular importance, as explained below.

It is thus, with regard to the stochiometry of the partial oxidation to give the desired target compound, generally necessary to use the molecular oxygen used as oxidant in at least stochiometric or in superstochiometric amounts (eg. to reoxidize the oxidic composition used as catalyst and to reduce carbon deposits).

On the other hand, for safety reasons, the proportion by volume of the molecular oxygen used as oxidant in the feed gas mixture must be below the oxygen limit concentration.

The oxygen limit concentration is that percentage by volume of molecular oxygen in the feed gas mixture below which, regardless of the proportions by volume of the other constituents of the feed gas mixture (in continuous operation, these proportions by volume can fluctuate unexpectedly as a result of faults), namely the organic compound to be partially oxidized and the inert diluent gas, combustion of the organic substance initiated by a local ignition source (for example, local overheating or spark formation in the reactor) is no longer able to spread from the ignition source through the feed gas mixture at the given pressure and temperature, so as to exclude the danger of an explosion.

Thus, the oxygen limit concentration of the feed gas mixture fixes the maximum proportion by volume of the organic compound to be partially oxidized (propylene) in the feed gas mixture and thus the achievable space-time yield of target product (cf. also EP-A 257 565, p. 5, lines 36/37).

Of course, the oxygen limit concentration of the feed gas mixture is influenced significantly by the type of constituents of the feed gas mixture, which is why the selection of the inert diluent gas (its composition) is of particular importance to the heterogeneously catalyzed gas-phase partial oxidation of propylene.

The classical methods of heterogeneously catalyzed gas-phase oxidation of propylene to acrolein and/or acrylic acid have no recirculation streams of inert diluent gas and generally recommend steam and/or nitrogen as inert diluent gas to avoid the explosive region (cf., for example, U.S. Pat. No. 4 147 885, column 1, lines 20 to 35, DE-A 20 56 614, page 2, last two lines, DE-B 20 09 172, column 4, lines 40 to 45, DE-A 22 02 734, p. 4, lines 18 to 22, DE-A 30 06 894, page 6, line 21 and DE-A 24 36 818, page 2, paragraph 3, with DE-A 20 56 614 attributing the particular suitability of steam as inert diluent gas to its relatively high molar heat capacity (page 4, paragraph 2, line 4), whereas DE-B 22 51 364 mentions the cost aspect of nitrogen as inert diluent gas (air as source of the oxidant) in respect of its frequent use.

DE-A 19 24 431 likewise concerns a gas-phase catalytic oxidation process for preparing acrylic acid from propylene without an inert gas recirculation stream. As suitable inert diluent gases, DE-A 19 62 431 mentions nitrogen, steam, carbon dioxide or saturated hydrocarbons.

DE-B 22 51 364 recommends, for a heterogeneously catalyzed gas-phase process for the partial oxidation of propylene to acrylic acid without an inert gas recirculation stream, steam as inert diluent gas, to which nitrogen or saturated hydrocarbons such as methane, propane or butane can be added. DE-A 14 68 429 recommends carbon dioxide, nitrogen, saturated hydrocarbons or steam as inert diluent gases in a process for the heterogeneously catalyzed gas-phase oxidation of propylene to acrylic acid without recirculation streams, with preference being given to steam.

However, all the examples of DE-A 19 62 431, DE-B 22 51 364 and DE-A 14 68 429 do not include any example in which a saturated hydrocarbon would even have been used as part of the inert diluent gas.

DE-A 30 06 894 likewise concerns, in a heterogeneously catalyzed gas-phase partial oxidation process for propylene, the problems of, on the one hand, preventing a runaway reaction and, on the other hand, achieving a productivity which is as high as possible (p. 2, lines 11 to 19). The solution recommended is to feed in the feed gas mixture at low catalyst activity and subsequently to successively increase the catalyst activity along the reaction coordinate.

Possible inert diluent gases mentioned in DE-A 30 06 894 are nitrogen, carbon dioxide and/or steam.

German Auslegeschrift 17 93 302 relates to a process of heterogeneously catalyzed gas-phase partial oxidation in which the inert diluent gas used is, after separating off the target product, the reaction off-gas containing the carbon oxides and water vapor produced in the reaction. DE-A 20 56 614 likewise addresses the problems of preventing explosion-like combustion processes in the heterogeneously catalyzed gas-phase partial oxidation of propylene (eg. p. 3, paragraph 2, last two lines). To avoid disadvantageous effects of the preferred diluent gas steam, DE-A 20 56 614 recommends recirculating the reaction off-gases largely freed of condensible gases, with partial or complete replacement of the water vapor, to the oxidation reactor as inert diluent gases and simultaneously feeding the feed gas mixture in at low catalyst activity and subsequently increasing the catalyst activity successively along the reaction coordinate. Since the oxidant "molecular oxygen" is fed in as a constituent of air, the effective inert diluent gases in the method of DE-A 20 56 614 are essentially nitrogen and carbon dioxide. The method of DE-A 24 36 818 corresponds, in terms of the inert diluent gases used, essentially to that of DE-A 20 56 614. The same applies to U.S. Pat. No. 4 147 885. DE-A 27 29 841 relates to a process for the heterogeneously catalyzed gas-phase oxidation of propylene to acrylic acid, which, owing to the use of a specific oxidation catalyst, makes it possible to use, in place of steam as inert diluent, a mixture of CO, $CO_2$, nitrogen and argon which is separated from the product gas mixture of the heterogeneously catalyzed partial oxidation and is recirculated to the feed gas mixture.

EP-B 253 409 (cf., in particular, p. 5, first three lines) and EP-A 257 565 teach, for avoiding an explosion risk in the heterogeneously catalyzed gas-phase partial oxidation of propylene, the use of those inert diluent gases which have an increased molar heat capacity $C_p$. Preference is here given, for example on page 4, lines 47 ff of EP-B 253 409 and on p. 5, lines 26 ff of EP-A 257 565, to mixtures of nitrogen, $CO_2$, methane, ethane, propane and steam. However, apart from the gases specified, it is also possible for helium, argon, other saturated hydrocarbon gases, $N_2O$ and carbon monoxide to be additionally present. Only its mean molar heat capacity is considered important for the action of the inert diluent gas.

Thus, in all examples, the inert diluent gas of the feed gas mixture comprises more than 55% by volume of $N_2$. Furthermore, EP-B 253 409 and EP-A 257 565 recommend recirculating the inert diluent gases present in the product gas mixture at least partially to the feed gas mixture.

British Patent No. 14 50 986 recommends, particularly because of its relatively high ability to absorb heat, the use of carbon dioxide as essentially the only inert diluent gas for avoiding the danger of explosion in the gas-phase catalytic oxidation for preparing acrylic acid from propylene.

EP-A 293 224 concerns a process for the heterogeneously catalyzed gas-phase oxidation of propylene to acrylic acid, in which the use of a gas mixture containing carbon dioxide, steam and saturated hydrocarbons having from 1 to 5 carbon atoms is recommended as inert gas to ensure that the process can be carried out safely (p. 3, lines 9 and 20 of EP-A 293 224). EP-A 293 224 considers the presence of carbon oxides in relatively high concentrations (page 3, line 57) and a relatively high molar heat capacity of the inert gas mixture (page 3, line 57) to be essential to the effectiveness of the inert gas mixture recommended in EP-A 293 224. EP-A 293 224 considers a further particular advantage of the procedure it recommends to be the fact that a considerable part of the inert gas mixture to be used can be obtained from the product gas mixture of the partial oxidation. In all examples, the inert gas mixture used in the feed gas mixture comprises steam and $CO_2$ in a total amount of at least 15% by volume, based on the inert gas mixture. EP-A 117 146 relates to a process for the heterogeneously catalyzed gas-phase partial oxidation of propylene to acrylic acid, with the propylene being generated by heterogeneously catalyzed dehydrogenation of propane. EP-A 117 146 presents it as a particular advantage that the product mixture of the propane dehydrogenation can be transferred without intermediate treatment to the oxidation stage and the inert constituents can subsequently be recirculated to the propane dehydrogenation stage. Similarly, the feed gas mixture in all examples includes an inert diluent gas comprising more than 15% by volume of steam.

A disadvantage of the continuous processes of the prior art for the heterogeneously catalyzed gas-phase oxidation of propylene to acrylic acid is that the inert diluent gases used in the feed gas mixtures are not satisfactory in respect of the oxygen limit concentrations associated therewith.

A further disadvantage of the procedure of EP-A 117 146 is that it is necessarily linked to propane as propylene source.

It is an object of the present invention to find a process for the continuous heterogeneously catalyzed gas-phase oxidation of propylene to acrolein, acrylic acid or a mixture thereof in an oxidation reactor whose feed gas mixture comprises, apart from propylene and molecular oxygen as oxidant, only at least one diluent gas which is essentially inert under the conditions of the heterogeneously catalyzed gas-phase oxidation, where, in continuous operation, at least a part of the essentially inert diluent gas constituents present in the product gas mixture is separated off therefrom and is reused as a constituent of the feed to the oxidation reactor which process does not have the above disadvantages of the processes of the prior art.

We have found that this object is achieved by a process for the continuous heterogeneously catalyzed gas-phase oxidation of propylene to acrolein, acrylic acid or a mixture thereof in an oxidation reactor whose feed gas mixture comprises, apart from propylene and molecular oxygen as oxidant, only at least one diluent gas which is essentially inert under the conditions of the heterogeneously catalyzed gas-phase oxidation, where, in continuous operation, at least a part of the essentially inert diluent gas constituents present in the product gas mixture is separated off therefrom and is reused as a constituent of the feed to the oxidation reactor, wherein the essentially inert diluent gas of the feed gas mixture in continuous operation comprises more than 85% by volume, preferably at least 90% by volume, better at least 95% by volume, even better at least 97% by volume, advantageously at least 98% by volume, preferably at least 99% by volume and best 100% by volume, of at least one saturated hydrocarbon having from 1 to 5 carbon atoms.

Suitable constituents of the inert diluent gas, other than the hydrocarbons having from 1 to 5 carbon atoms, are, for example, $CO_2$, CO, $N_2$, $H_2O$, higher saturated hydrocarbons and/or nobel gases such as He and Ar.

The mean molar specific heat $C_p$ of the inert diluent gas of the feed gas mixture is advantageously in the range from 10 to 50 cal/mol·K, preferably from 10 to 35 cal/mol·K (at 1 atm. and 300° C.).

The inert diluent gas of the feed gas mixture preferably contains no steam.

Suitable saturated hydrocarbons having from 1 to 5 carbon atoms are methane, ethane, propane, n-butane, iso-butane, n-pentane, iso-pentane, neo-pentane and mixtures of said hydrocarbons. Among the abovementioned hydrocarbons, methane, propane and mixtures thereof are preferred for use as constituents of the diluent gas. This applies particularly to methane which is, when the reaction is carried out in a tube bundle reactor, both particularly advantageous for avoiding local overheating (hot spots) along the contact tubes and displays a high degree of inertness. Propane is useful insofar as when it is not completely inert, it is normally converted predominently into propylene, acrylene and/or acrylic acid.

These teachings are the result of comprehensive and systematic research work. They are based on the recognition that the oxygen limit concentration of a feed gas mixture comprising molecular oxygen, inert diluent gas and propylene (the proportion of molecular oxygen decreases along the reaction coordinate) is influenced less by the molar heat capacity $C_p$ of the inert diluent gas than by the inert diluent gas itself being essentially combustible, lower organic compound, with the simultaneous requirement of inertness necessitating the restriction to lower saturated hydrocarbons.

The feature "combustible" here indicates compounds whose mixtures with air at an initial pressure of 1 bar and an initial temperature of 50° to 100° C. have an upper and a lower explosive limit (ignition limit), with the determination of the explosive limits being based on measurement in the standard apparatus as described by W. Berthold et al. in *Chem.-Ing. Tech.* 56 (1984) No. 2, pp. 126–127 ($N_2$, $CO_2$ and $H_2O$ are, for example, not combustible compounds).

In this context, explosive limits are the following limit values in accordance with DIN 51 649: In a mixture of air and a combustible gas, the velocity at which, under prescribed initial conditions, combustion (ignition, explosion) initiated by a local ignition source (eg. glowing platinum wire) spreads is dependent on the combustible gas content. It is greatest at a particular content. Either decreasing or increasing the combustible gas content reduces the combustion velocity until finally, at a lower and an upper limit value for the combustible gas content, the combustion reaction just no longer spreads out from the ignition source. These two limit values are the lower explosive limit and the upper explosive limit, the range of combustible gas content lying between them is the explosive region (ignition region).

The higher the proportion of the lower saturated hydrocarbons in the inert diluent gas of the feed gas mixture for the heterogeneously catalyzed gas-phase oxidation of propylene, the more safely this reaction can be carried out even with increased proportions by volume of the reactants.

A particular aspect of the process of the invention is that the lower saturated hydrocarbons used according to the invention as inert diluent gas constituents of the feed gas mixture are, unlike the inert diluent gas constituents such as $N_2$, $H_2O$ and $CO_2$ preferred in the prior art, materials of value owing to their combustibility and can be used, for example, for energy generation. An essential feature of the process of the invention is therefore that at least a part of the saturated hydrocarbons having from 1 to 5 carbon atoms present in the product gas mixture as inert diluent gas constituents is separated off from the gas mixture and is recirculated into the feed to the oxidation reactor as constituent of a new feed gas mixture (i.e. it is reused).

Preferably, in continuous operation, at least 50% by volume of the saturated hydrocarbons having from 1 to 5 carbon atoms present in the product gas mixture are recirculated. This proportion is preferably at least 75% by volume, better at least 90 or 95% by volume and even better at least 98 or 99 or 100% by volume.

The abovementioned recirculation is a prerequisite for the economical operation of the process of the invention. For the purposes of this recirculation, note should be taken of the fact that the saturated hydrocarbons having from 1 to 5 carbon atoms generally have to be separated not only from the target product present in the product gas mixture, but also from byproducts present therein (at least partially). This also applies when the latter are gases such as $CO_2$ or $H_2O$ which are inert in relation to the gas-phase oxidation of the propylene, since these may otherwise accumulate in the diluent gas of the feed gas mixture during the course of continuous operation. Of course, for the purposes of the process of the invention, unreacted starting material and/or intermediate still present in the product gas mixture can also be separated from the latter and recirculated to the oxidation reactor.

The separation processes to be used for this purpose, such as fractional condensation or absorption and extraction processes, are known to those skilled in the art and require no further explanation. The work-up and separation of the desired target product is likewise carried out in a manner known per se.

As source of the molecular oxygen required as oxidant for the purposes of the process of the invention, air has only limited suitability, since molecular oxygen occurs in air only in association with $N_2$.

This means that preference is given to taking the oxygen required for the process of the invention from an essentially pure oxygen source.

In summary, the difference in the process of the invention from the processes of the prior art is essentially that, under otherwise identical reaction conditions, when using the proportion according to the invention of saturated hydrocarbons having from 1 to 5 carbon atoms in the inert diluent gas used in the feed gas mixture, the continuous heterogeneously catalyzed gas-phase oxidation of propylene to acrolein, acrylic acid or a mixture thereof, particularly with relatively high proportions by volume of reactants in the feed gas mixture, can be carried out with increased safety (the feed of molecular oxygen can also fluctuate in continuous operation as a result of unexpected faults), which forms the basis for increased space-time yields. This is illustrated below by some examples. In conclusion, it may be affirmed that, for the heterogeneously catalyzed gas-phase oxidation of propylene to acrolein, the propylene/molecular oxygen feed in the feed gas mixture is selected such that the volume ratio is 1 (propylene): from 1 to 3 (molecular oxygen), preferably 1 (propylene): from 1.5 to 2 (molecular oxygen). As already mentioned, the oxygen excess has an advantageous effect on the kinetics of the gas-phase oxidation and on the life of the catalyst. The thermodynamic conditions are essentially not influenced thereby, since the heterogeneously catalyzed gas-phase partial oxidation of the invention is subject to kinetic control. The above propylene/molecular oxygen feed is advantageously also selected for the two-stage gas-phase oxidation of propylene to acrylic acid (eg. in an oxidation reactor comprising two oxidation reactors in series). In general, the product gas mixture leaving the first stage (the first oxidation reactor) is here transferred without intermediate treatment to the second oxidation reactor. Advantageously, the second oxidation stage (the second oxidation reactor) is additionally fed with molecular oxygen as oxidant. The amount of molecular oxygen additionally fed in is preferably selected in such a way that the feed gas mixture to the second oxidation stage (the second oxidation reactor) has an $O_2$ content which is at least stochiometric to about three times stochiometric. The oxygen is here likewise preferably taken from an essentially pure oxygen source. The safety of the second oxidation stage (the second oxidation reactor) can be additionally increased by separating water vapor and $CO_2$ formed as byproducts in the first oxidation stage from the product gas mixture leaving the first oxidation stage (the first oxidation reactor), before transferring it to the second oxidation stage (into the second oxidation reactor). It may be affirmed that, in accordance with the process method of the invention, it is safer to handle feed gas mixtures whose propylene feed is >30% by volume (with favorable selection of the inert diluent gas up to 40 or 45% by volume), based on the feed gas mixture.

Favorable feed gas mixtures are those which, in continuous operation, comprise from 15 to 30% by volume of propylene, from 30 to 45% by volume of oxygen and from 40 to 55% by volume of inert diluent gas according to the invention.

We claim:

1. A process for the continuous heterogeneously catalyzed gas-phase oxidation of propylene to acrolein, acrylic acid or a mixture thereof in an oxidation reactor whose feed gas mixture comprises, apart from propylene and molecular oxygen as oxidant, only at least one diluent gas which is essentially inert under the conditions of the heterogeneously catalyzed gas-phase oxidation, where, in continuous operation, at least a part of the essentially inert diluent gas constituents present in the product gas mixture is separated off therefrom and is reused as a constituent of the feed to the oxidation reactor, wherein the essentially inert diluent gas of the feed gas mixture in continuous operation comprises more than 85% by volume of at least one saturated hydrocarbon having from 1 to 5 carbon atoms.

2. A process as claimed in claim 1, wherein the essentially inert diluent gas of the feed gas mixture in continuous operation comprises at least 90% by volume of at least one saturated hydrocarbon having from 1 to 5 carbon atoms.

3. A process as claimed in claim 1, wherein the essentially inert diluent gas of the feed gas mixture in continuous operation comprises at least 95% by volume of at least one saturated hydrocarbon having from 1 to 5 carbon atoms.

4. A process as claimed in claim 1, wherein the essentially inert diluent gas of the feed gas mixture in continuous operation comprises at least 97% by volume of at least one saturated hydrocarbon having from 1 to 5 carbon atoms.

5. A process as claimed in claim 1, wherein the essentially inert diluent gas of the feed gas mixture in continuous operation comprises at least 98% by volume of at least one saturated hydrocarbon having from 1 to 5 carbon atoms.

6. A process as claimed in claim 1, wherein the essentially inert diluent gas of the feed gas mixture in continuous operation comprises at least 99% by volume of at least one saturated hydrocarbon having from 1 to 5 carbon atoms.

7. A process as claimed in claim 1, wherein the essentially inert diluent gas of the feed gas mixture in continuous operation consists of 100% by volume of at least one saturated hydrocarbon having from 1 to 5 carbon atoms.

8. A process as claimed in claim 1, wherein the saturated hydrocarbon comprises at least 50 mol % of methane.

9. A process as claimed in claim 1, wherein the saturated hydrocarbon comprises at least 50 mol % of propane.

10. A process as claimed in claim 1, wherein the continuous heterogeneously catalyzed gas-phase oxidation of propylene to acrylic acid is carried out in an oxidation reactor comprises ing two oxidation reactors connected in series with the feed gas mixture being fed to the first oxidation reactor and propylene being oxidized essentially to acrolein in this reactor, the product gas mixture of the first oxidation reactor subsequently being conveyed without intermediate treatment to the second oxidation reactor and the latter being fed with the amount of molecular oxygen required for the further oxidation of the acrolein to acrylic acid.

* * * * *